(12) United States Patent
Mazzanti

(10) Patent No.: US 8,309,058 B2
(45) Date of Patent: Nov. 13, 2012

(54) METHOD FOR OBTAINING HIGHLY LUMINESCENT LANTHANIDE COMPLEXES

(75) Inventor: Marinella Mazzanti, St. Martin le Vinoux (FR)

(73) Assignee: Commissariat a l'Energie Atomique, Paris (FR)

( * ) Notice: Subject to any disclaimer, the term of this patent is extended or adjusted under 35 U.S.C. 154(b) by 1069 days.

(21) Appl. No.: 12/066,828

(22) PCT Filed: Sep. 12, 2006

(86) PCT No.: PCT/FR2006/002089
§ 371 (c)(1),
(2), (4) Date: Apr. 2, 2008

(87) PCT Pub. No.: WO2007/031640
PCT Pub. Date: Mar. 22, 2007

(65) Prior Publication Data
US 2008/0227962 A1    Sep. 18, 2008

(30) Foreign Application Priority Data
Sep. 15, 2005 (FR) ................................. 05 09444

(51) Int. Cl.
*A61B 10/00* (2006.01)
*A61B 5/00* (2006.01)
*A61B 8/00* (2006.01)

(52) U.S. Cl. ............. 424/9.6; 424/9.2; 424/9.42; 534/15

(58) Field of Classification Search .................... 424/9.6
See application file for complete search history.

(56) References Cited

OTHER PUBLICATIONS

Chatterton et al. Angew. Chem. Int. Ed., 2005, 44, 7595-7598.*
Chatterton et al. Angew. Chem. Int. Ed. 2005, 7595-7598.*
Chatterton, N., Gateau C.; "The effect of pyridinecarboxylate chelating groups on the stability and electronic relaxation of gadolinium complexes"; Dalton Transactions, 2005, pp. 1129-1135, XP002397230.
Platas-Iglesias C., Mato-Iglesias M. "Lanthanide Chelates Containing Pyridine Units with Potential Application as Contrast Agents in Magnetic Resonance Imaging"; Chemistry—A European Journal; 2004; pp. 3579-3590.

* cited by examiner

*Primary Examiner* — Michael G Hartley
*Assistant Examiner* — Sean R Donohue
(74) *Attorney, Agent, or Firm* — Young & Thompson

(57) ABSTRACT

The invention concerns a transition metal coordination complex of general formula (I) $\{[M(X)]C(H_2O)_n\}p$ wherein: M represents an element belonging to the lanthanide group; and L represents a decadentate chromophore ligand of general formula (II). R1, R2, R3 and R4 independently represent hydrogen or an alkyl or aryl radical. A1, A2, A3 and A4 independently represent a structure of general formula (III). U1, U2 and U3 independently represent C or N, and R5, R6 and R7 independently represent hydrogen, an alkyl or aryl radical. Y represents C, O, S, P or N, and m is an integer representing free valences of Y. R8 represents independently hydrogen, an alkyl or aryl radical. X represents a counter-ion, and n represents hydrating water molecules. p represents monomers. $H_2O$ represents the hydrating water molecules. The invention also concerns a method for preparing such a ligand by reaction between a 6-chloromethylpyridine-2-carboxylate ethyl ester and ethylenediamine in organic medium.

4 Claims, 8 Drawing Sheets

METHOD FOR OBTAINING HIGHLY LUMINESCENT LANTHANIDE COMPLEXES

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to new complexes for co-ordinating a transition metal, in particular lanthanides, and their applications in the medical field.

2. Description of Related Art Including Information Disclosed Under 37 CFR 1.97 and 37 CFR 1.98

The unique electronic properties of the lanthanide ions, such as their long life luminescence and their well-defined emission spectrum, turn these compounds into an ideal tool for usage in the medical field.

Indeed, the use of the lanthanide complexes, enables to distinguish the fluorescence considered as a background noise and the signal targeted. Thus said complexes are often used, in the design of detectors, as spectroscopic and luminescent probes for solving structural and analytical problems and as fluorescence imaging systems.

According to the rules laid down by the "International Union of Pure and Applied Chemistry" (IUPAC), by lanthanide is meant the series of the chemical elements ranging from Cerium (Z=58) to Lutecium (Z=71). By including Lanthane (Z=57), these elements are called lanthonoid. The expression "rare earth" applies to the lanthanoid together with Scandium (Z=21) and Yttrium (Z=39), the latter having similar chemical properties. In practice, the designations as lanthanides, lanthanoid and rare earth are used for describing these elements.

Generally, the lanthanides form their most stable compounds when they are in +3 oxidation state. The electronic structure of the $Ln^{III}$ ions is that of the xenon for the $La^{III}$ and then corresponds to the filling of the orbitales 4f14 up to $[Xe]4f^{14}$ for the $Lu^{III}$.

Currently, most studies performed with lanthanide complexes have been oriented towards establishing light-emitting probes including long life visible light transmitters, in particular $Eu^{III}$ and $Tb^{III}$, or transmitters in the near-infrared spectrum, such as the $Pr^{III}$, $Er^{III}$ $Yb^{III}$ or the $Nd^{III}$.

However, as the prohibited transition 4f-4f, so-called Laporte prohibition, prevents the direct excitation of the lanthanides, the latter must be performed using certain adequate organic chromophores.

In the meaning of the invention a "chromophore" is a molecule capable of absorbing the UV/visible light and of transferring to the metallic centre, which, by accepting such energy, becomes "excited" to a state capable of transmitting light (aerial effect). Preferably a "chromophore", also called "aerial", corresponds to an atom moiety liable to partake of long enough a sequence with double links matched in an organic molecule. An aromatic cycle carrying delocalisable π electrons will be considered as a chromophore in the sense of the present invention.

Besides, for practical reasons in physiological conditions, the lanthanide ions must be incorporated in highly stable complexes. Indeed, the efficiency of the energy transfer from the ligand on the lanthanide is decisive for the design of highly performing probes.

Moreover, so as to obtain high quantal throughput, non-radiative de-energisation should be prevented, or at least minimised, of the excited state of the lanthanide ion further to an interaction of the metal with the surrounding water molecules.

The incorporation of the chromophores in certain polydentate ligands studied to that end leads to greater stability of the lanthanide chelates in solution, enabling greater protection of the metal from the water molecules.

However, the tendency of the lanthanide ions to adopt a high co-ordination number and their lack of stereochemical selectivity turn the design of these ligands into a major challenge.

A strategy, which has been adopted by different research groups, is based upon a "tripod" structure of a ligand in order to organise three trivalent binding units in ennea-coordinated $Ln^{III}$ complexes.

This approach has led, in some cases, to an efficient protection of the metal from the surrounding water molecules, but synthesis difficulties make it little interesting.

The preparation of the polydentate ligands, enabling the arrangement of four bidentate moieties around a lanthanide ion, has less drawn the attention of the researchers in spite of the excellent luminescence of observed for tetra complex obtained from bidentate chromophore ligands, such as quinolinates or tropolonates.

Recently, octadentate ligands including four divalent chromophores have led to lanthanide complexes with energy emissions in the ultra-violet zone (UV) or in the near-infrared spectrum (NIR) which are very efficient.

However, the structure of these complexes has not been elucidated as yet, and the fact that the part of the structure of the ligand binding the bidentate units together is highly flexible, involves that the protection of the central metal is far from optimum.

BRIEF SUMMARY OF THE INVENTION

The aim of the present invention is to provide new complexes for co-ordinating a transition metal, in particular lanthanides, which remedy the shortcomings aforementioned, particularly as regards their stability in aqueous medium and their flexibility.

Another aim of the present invention is to provide new complexes for co-ordinating a transition metal, in particular lanthanides, which are easy to prepare and which exhibit high luminescence quantal throughput.

Another aim of the present invention is to provide new co-ordinating complexes exhibiting chemical and photophysical features liable to be used in the medical and biotechnological field.

Other aims and advantages of the invention will appear in the following description solely given by way of example and without being limited thereto.

The present invention relates to a complex for co-ordinating a transition metal of the general formula (I)

$\{[M(L)]X(H_2O)_n\}_p$ wherein:

M represents an element belonging to the group of the lanthanides,
L represents a decadentate chromophore ligand of the general formula (II):

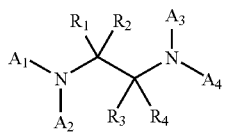

Wherein,
$R_1$, $R_2$, $R_3$ and $R_4$ correspond independently to hydrogen, an alkyl or aryl radical,
$A_1$, $A_2$, $A_3$ and $A_4$ correspond independently to a structure of the general formula (III):

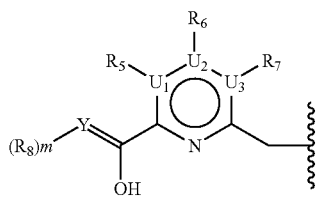

Wherein,
$U_1$, $U_2$ and $U_3$ correspond independently to a C or an N,
$R_5$, $R_6$ and $R_7$ correspond independently to hydrogen, an alkyl or aryl radical,
Y corresponds to a C, O, S, P or N,
m is an integer corresponding to the number of free valencies of Y,
$R_8$ corresponds independently to hydrogen, an alkyl or aryl radical,
X represents a counter-ion,
n represents the number of molecules of hydration water,
p corresponds to the number of monomers,
$H_2O$ represents the molecules of hydration water.

An alkyl radical may be optionally mono- or polysubstituted, linear, branched or cyclic, saturated or unsaturated, in C1-C20, preferably in C1-C10, wherein the substituent(s) are liable to contain one or several heteroatoms such as N, O, F, Cl, P, Si or S. Among such alkyl radicals, the methyl, ethyl, propyl, isopropyl, butyl, isobutyl, tert-butyl and pentyl radicals may also be mentioned. Among the unsaturated alkyl radicals the ethenyls, propenyls, isopropenyls, butenyls, isobutenyls, tert-butenyls, pentenyls and acetylenyls may also be quoted.

An aryl radical may be an aromatic or heteroaromatic carbonous structure, mono- or polysubstituted, formed of one or several aromatic or heteroaromatic cycles each comprising from 3 to 8 atoms, wherein the heteroatom may be N, O, P or S.

Optionally, when the alkyl or aryl radicals are polysubstituted, the substituents may be different from one another. Among the substituents of the alkyl and aryl radicals, one may in particular mention the halogen atoms, the alkyl, haloalkyl, aryl substituted or not, heteroaryle substituted or not, amino, cyano, azido, hydroxy, mercapto, ceto, carboxy, etheroxy and alcoxy such as methoxy groups.

The present invention also relates to a preparation method of a ligand as described above, characterised in that it includes the reaction of a diamine of the general formula (IV):

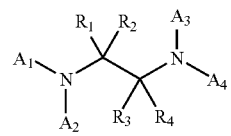

Wherein,
$R_1$, $R_2$, $R_3$ and $R_4$ are as defined above,
and of at least one compound of the general formula (V)

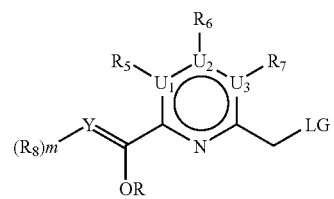

Wherein,
Y, $R_5$, $R_6$, $R_7$, $R_8$, $U_1$, $U_2$ and $U_3$ are as defined above,
R corresponds to an alkyl or an aryl,
LG represents an outgoing group liable to undergo a nucleophilic substitution from the diamine.

The present invention relates moreover to a preparation method of co-ordinating complexes characterised in that it comprises the reaction between a lanthanide salt and a ligand in aqueous medium, as well their usage in the medical field, such as in diagnostic imaging, radiotherapy, and in the design of neutron detectors, screens for X-rays, of the probes for imaging and bio-assays, diodes, optical fibres etc.

BRIEF DESCRIPTION OF THE SEVERAL VIEWS OF THE DRAWINGS

The invention will be understood better when reading the following description, accompanied by the appended drawings.

DETAILED DESCRIPTION OF THE INVENTION

Figure 1:
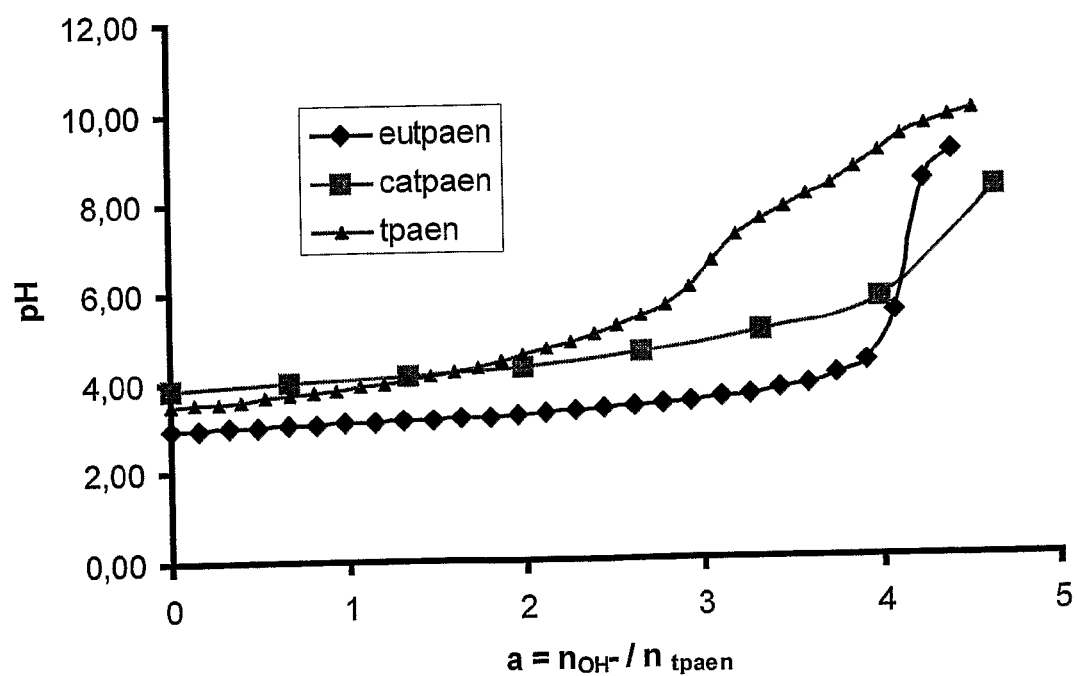
FIG. 1 is a graph illustration of titration curves.

The present invention relates first of all to a complex for co-ordinating a transition metal of the general formula (I):

$\{[M(L)]X(H_2O)n\}p$ wherein:
M represents an element belonging to the group of the lanthanides,
L represents a decadentate chromophore ligand of the general formula (II):

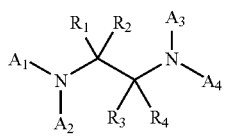

Wherein,
$R_1$, $R_2$, $R_3$ and $R_4$ correspond independently to hydrogen, an alkyl or aryl radical,
$A_1$, $A_2$, $A_3$ and $A_4$ correspond independently to a structure of the general formula (III):

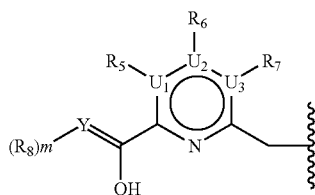

Wherein,
$U_1$, $U_2$ and $U_3$ correspond independently to a C or an N,
$R_5$, $R_6$ and $R_7$ correspond independently to hydrogen, an alkyl or aryl radical,
Y corresponds to a C, O, S, P or N,
m is an integer corresponding to the number of free valencies of Y,
$R_8$ corresponds independently to hydrogen, an alkyl or aryl radical,
X represents a counter-ion,
n represents the number of molecules of hydration water,
p corresponds to the number of monomers,
$H_2O$ represents the molecules of hydration water.

According to the physical state adopted (crystallised or dissolved for instance), the complex may include so-called co-ordinating solvent molecules, it is in particular water molecules.

According to a particular embodiment of the present invention, the element belonging to the group of the lanthanides is Europium (Eu), or Cerium (Ce) or Terbium (Tb).

Advantageously $R_1$, $R_2$, $R_3$ and $R_4$ will be independently hydrogen, methyl or ethyl, preferably they will all be hydrogen.

The inventors consider that it is preferable that $A_1$, $A_2$, $A_3$ and $A_4$ are identical, since this enables to keep the symmetry of the molecule, thereby increasing the aerial effect and preventing the spurious energy transfers.

It is also preferable that Y is sulphur or oxygen, and in such a case m is equal to 0.

Generally speaking it is preferable to choose carbonous aromatic groups, the inventors consider that it is advantageous that $U_1$, $U_2$ and $U_3$ are carbons.

The preferred complexes according to the invention are those for which $R_5$, $R_6$ and $R_7$ are independently hydrogen or an alkyl radical, such as methyl or ethyl, advantageously they are identical and preferably correspond to hydrogens.

One of the advantages of such type of co-ordinating complex lies in their stability in aqueous medium which enables their usage in physiological and biological media and, hence, in the medical field.

Calcium, metal known by its significance in certain biological systems, is less complexed than the lanthanides by the ligand of the present invention. This selectivity is very significant for medical application.

In a particular embodiment of the present invention said ligand comprises four bidentate chromophores connected by an ethylenediamine skeleton.

According to a particular embodiment of the present invention, said ligand comprises four pyridinecarboxylate moieties bound by an ethylenediamine skeleton.

According to a particular embodiment of the present invention, the ligand including the four pyridinecarboxylate moieties is N,N,N',N'-tetrakis[(6-carboxypyridine-2-yl)methyl]-ethylenediamine.

One of the advantages of the ligands according to the invention and particularly those of type N,N,N',N'-tetrakis[(6-carboxypyridine-2-yl)methyl]-ethylenediamine, lies in that they include ten electron donor atoms and a "skeleton" formed of an ethylene diamine bridge perfectly adapted to the complexing of a lanthanide, in particular Eu, Tb and Ce, but also the lanthanides with emission in the infrared, providing highly effective protection of the central metal with respect to the surrounding water molecules, in particular water molecules of the solvent. Because of the protection, the complexes, in particular of $Eu^{III}$ and $Tb^{III}$ with the ligand N,N,N',N'-tetrakis[(6-carboxypyridine-2-yl)methyl]-ethylene diamine, exhibit long life water luminescence, associated with high solubility and high stability.

According to the present invention, the counter-ion X present in the complexes is an element belonging to the group 1A of the periodic table of the elements, and more particularly potassium. The way the counter-ion K+ is bound to the complexes of Europium and of Cerium, leads to two different structures, a monomeric structure in the case of the complex with Europium and a dimeric structure in the case of the complex with Cerium.

The value of p varies according to the type of complex and represents the number of monomers each forming complexes, p is equal to one for a monomeric complex as it is the case for Europium and p is equal to 2 for a dimeric complex as it is the case for Cerium (see the examples of embodiment).

Similarly the value of n is function of the complex considered and of the atmosphere and temperature conditions. Typically this number will be ranging between 0 and 20 for a non-dissolved complex.

The invention also relates to The preparation of a decadentate chromophore ligand as described above, by reaction of a diamine of the general formula (IV):

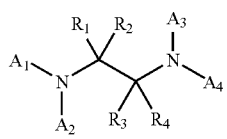

Wherein,
$R_1$, $R_2$, $R_3$ and $R_4$ are as defined above,
and of at least one compound of the general formula (V)

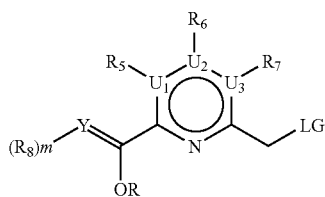

Wherein,

Y, $R_5$, $R_6$, $R_7$, $R_8$, $U_1$, $U_2$ and $U_3$ are as defined above,

R corresponds to an alkyl or an aryl.

LG represents an outgoing group liable to undergo a nucleophilic substitution from the diamine.

Advantageously the man of the art will select LG among most labile outgoing groups and in particular those reacting with amines. The inventors consider that Cl, Br, I, -OTf, -OTs, CN may be used advantageously.

The moiety R will be preferably selected among the methyl, ethyl, propyl, isopropyl, butyl, isobutyl, benzyl radicals and among the heteroalkyls in particular the radicals used as protective groups of the alcohol functions like the trimethylsiyl (TMS) or terbutyledimethylesilyl (TBDMS).

The method according to the invention may be provided in any suitable solvent, in particular organic solvents such as acetonitrile, tetrahydrofuran, chloroform, dichloromethane, carbon tetrachloride, toluene.

The preferred operating conditions are easily determined by the man of the art from the substituents that he will have chosen for its compounds, wherein the substitution reaction by an amine is well-known in the art. It is preferable to conduct the reaction in the presence of a base to facilitate the reaction of the amine, then to acidify the reactive medium for regenerating the alcohol protected by the group R.

Thus, according to the method, by reaction between ethyl ester of the 6-chloromethylpyridine-2-carboxylate and ethylenediamine, preferably in organic medium, the decadentate ligand N,N,N',N'-tetrakis[(6-carboxypyridine-2-yle)methyl]-ethylene diamine, also designated in the present invention by $H_4$tpaen, is easily obtained in five steps with a final throughput of 26.0%.

Schematically, the reaction may be described as follows:

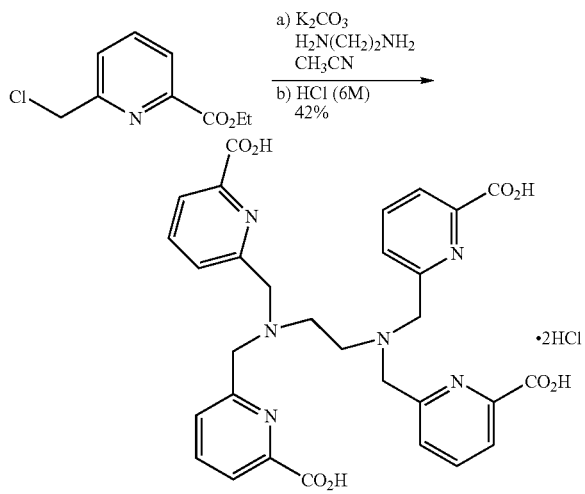

The preparation of the ligand $H_4$tpaen is simple, may be used at large scale and may be easily modified for anchoring the complex with certain functional moieties capable of binding to biomolecules in order to develop markers for luminescence imaging.

The ligand N,N,N',N'-tetrakis [(6-carboxypyridine-2-yl) methyl]-ethylene diamine may be prepared as follows.

Under an argon atmosphere, freshly distilled ethylenediamine (250 mL, 3.6 mmol) and anhydrous $K_2CO_3$ (2.04 g, 14.8 mmol) are successively added to an ethyl ester solution of the 6-chloromethylpyridine-2-carboxylate (2.95 g, 14.8 mmol) in anhydrous acetonitrile (50 mL). After filtration and evaporation of the solvent a yellow oil is obtained.

After re-integration in dichloromethane the solution formed is washed twice with water (100 mL) and dried on anhydrous $Na_2SO_4$. After evaporation of the solvent, the yellow oil obtained is used without any other purification.

For regenerating the acid function, the raw product (2.56 g) dissolved in an aqueous solution of HCl 6M (40 mL) is raised to reflux overnight. After evaporation of the solvent up to 5 mL, the solution is cooled down to 5° C. overnight. The precipitate is collected by filtration, washed with a solution of HCl M then vacuum dried. 1.37 g $H_4$tpaen.6HCl.$5H_2O$ are thus obtained with a 42% throughput.

The elementary analysis of the $H_4$tpaen.6HCl.$5H_2O$ is as follows: MM=909.33, $C_{30}H_{44}N_6O_{13}Cl_6$: C, 39.42; H 4.88; N 9.24; found C, 39.49; H 4.90; N 9.24.

The RMN spectra of the $H_4$tpaen are as follows:

$^1$H RMN ($D_2O$, 400 MHz, 298 K, pH=5): δ 3.57 (s, 4H, $NCH_2CH_2N$), 4.36 (s, 8H, $NCH_2$py), 7.48 (d, 4H, CH), 7.77 (d, 4H, CH), 7.84 (t, 4H, CH), $^{13}$C RMN ($D_2O$, 100 MHz): δ=51.6 ($CH_2$); 56.4 ($CH_2$); 57.8 ($CH_2$); 125.8 (CHpy); 128.4 (CHpy); 142.9 (CHpy); 147.4 (Cpy); 152.0 (Cpy); 166.4 (COOH); 172.1 (COOH).

The present invention relates moreover to a preparation method of a co-ordinating complex by reaction of a lanthanide salt with a ligand in aqueous medium.

Advantageously, the salt of a lanthanide is lanthanide chloride.

The ligand will be advantageously as described above.

In a particular embodiment of the present invention the lanthanide is Europium (Eu), Cerium (Ce) or Terbium (Tb), advantageously the lanthanide will be selected among the lanthanides with emission in the infrared.

The water soluble complexes, obtained from the ligand N,N,N',N'-tetrakis[(6-carboxypyridine-2-yl)methyl]-ethylene diamine, are isolated with a throughput ranging between 50 and 60% after reaction of said ligand with a hexa hydrated lanthanide chloride, in particular with Cerium or Europium and after adjustment of the pH to 6.

By way of example, not limited thereto, the Europium and Cerium complexes may be prepared by reaction between Europium trichloride or cerium trichloride and the ligand N,N,N,N',N'-tetrakis[(6-carboxypyridine-2-yl)methyl]-ethylene diamine.

These complexes may be prepared as follows.

A solution of $CeCl_3.7H_2O$ or of $EuCl_3.6H_2O$ (0.138 mmol) in water (0.5 mL) is added to a solution of N,N,N',N'-tetrakis [(6-carboxypyridine-2-yl)methyl]-ethylene diamine (0.138 mmol) at a pH of 5, adjusted by the addition of KOH (0.2 M) in water (6 mL). The solution thus obtained is stirred at room temperature for 2 hours and the pH is adjusted to 6 par the further addition of KOH (0.2 M).

After evaporation of water, the solid obtained is picked up in EtOH (5 mL) and the solution is filtered to eliminate insoluble salts. The solvent is evaporated and the residue picked up in water.

Slow evaporation over 5 days of the aqueous solution (1 mL) of the solid enables to obtain the complex ([Eu(tpaen)]K in the form of a white solid and the complex ([Ce(tpaen)]K in the form of a yellow solid with a throughput ranging between 50 and 60%.

The chemical and physical features of these complexes are as follows:

[Eu(tpaen)]: $^1$H RMN (D$_2$O, 400 MHz, 298 K, pD=6.9): δ−2.07 (s br, 2H, H$_6$/H$_6$,), −1.11 (s br, 2H, H$_4$'), −0.99 (s br, 2H, H$_4$), 3.48 (s br, 2H, H$_5$), 4.28 (s br, 2H, H$_5$'), 4.41 (d br, 2H, H$_3$), 5.43 (d br, 2H, H$_3$), 5.65 (s br, 2H, H$_1$), 5.79 (s br, 2H, H$_1$), 5.96 (br, 2H, H$_2$'), 6.53 (br, 2H, H$_2$), 8.40 (br, 2H, H6/H$_6$').

[Ce(tpaen)]: $^1$H RMN (D$_2$O, 400 MHz, 298 K, pD=5.4): δ−2.03 (s br, 2H, H6/H6'), 0.09 (s br, 2H, H$_5$'), 1.18 (s br, 2H, H$_6$/H$_6$,), 3.25 (d, 2H, H$_4$), 3.51 (d, 2H, H$_4$), 5.44 (s br, 2H, H$_5$), 7.97 (d, 2H, H$_3$), 8.10 (d, 2H, H$_3$,), 8.45 (d, 2H, H$_1$), 8.91 (t, 2H, H$_2$), 8.94 (d, 2H, H$_1$), 9.04 (t, 2H, H$_2$').

The crystallographic data for Eu(tpaen)] K(H$_2$O)$_3$. 4H$_2$O: C30H38Eu KN6O15, M=913.7, Monoclinical, spatial group P2 (1)/n, a=11.995(2) b=14.539(3), c=21.407(5) Å, β=106.186(3) V=3585.2(12) Å$^3$, Z=4, p$_c$=1.693 g cm$^{-3}$, μ=1.944 mm$^{-1}$, T=298 K. From the 12504 reflections collected, 5133 were unique (R$_{int}$=0.0192). The treatment of the data has converged to R$_1$=0.0296, wR2=0.0667. Max/min of residual density 0.693 and −0.528 eÅ$^{-3}$.

The crystallographic data for {[Ce(tpaen)] K(H$_2$O)$_3$}$_2$. 16H$_2$O, C30H46 CeKN6O19, M=973.95, Monoclinical, spatial group P2(1)/c, a=11.7615(10) b=14.5931(12), c=22.965 (2) Å, β=101.640(1) V=3860.7(6) Å$^3$, Z=4, p$_c$=1.676 g cm$^{-3}$, μ=1.374 mm$^{-1}$, T=193 K. From the 12929 reflections collected, 7459 were unique (R$_{int}$=0.0310). The treatment of the data has converged to R$_1$=0.0430, wR2=0.1340. Max/min of residual density 1.055 and −2.462 eÅ−3.

Besides, five de-protonation constants [pK$_{a1}$=2.8 (1), pK$_{a2}$2=3.2 (1), pK$_{a3}$=3.9 (2), pK$_{a4}$=5.1 (1) and pK$_{a5}$=7.8 (1)] may be determined for the ligand H$_6$tpaen by potentiometric titration as well the stability constants of the corresponding complexes of Eu$^{III}$ and of Ca$_{II}$ [log β$_{EuL}$=15.3(3) for the complex of Eu$^{III}$ and log β$_{CaL}$=8.5 (5)]. FIG. 1 shows the titration curves for the ligand H$_6$tpaen (▲), for the complex Eutpaen (◇) and for the complex Catpaen (■).

The values of pEu=15.7, pGd=15.0 and pCa=8.5 {−log [M]|$_{free}$ at a pH of 7.4, [M]$_{total}$=1 μM, and [tpaa]$_{total}$=10 μM), when they are compared with the value of pEu=14.0 for tetra acetic diamine ethylene acid (EDTA) show that the ligand tpaen forms lanthanide complexes with sufficient stability for their in vivo usage and also show good selectivity regarding Europium with respect to calcium.

For potentiometric titration, the solutions of the complex of Eu(III) may be prepared by dissolution of a determined amount of EuCl$_3$.6H$_2$O in water. The de-protonation constants of H$_6$tpaen are given by Kai=[H6-iL]$^{2-1}$/[H$_5$–iL]$^{1-i}$ [H]$^+$, and as already mentioned previously, the values obtained are pK$_{a1}$=2.8(1), pK$_{a2}$=3.2(1), pK$_{a3}$=3.9(2), pK$_{a4}$4=5.1(1) and pK$_{a5}$=7.8(1).

The exact concentration of the ion Eu$^{3+}$ could be determined by colorimetric titration in an acetate buffer (pH=4.5), using as a reference a solution of H$_2$Na$_2$edta and orange xylenol as an indicator.

The solutions of Ca(II) could be prepared by dissolution of CaCl$_2$ in water. The exact concentration of the ion Ca$^{2+}$ can be determined by colorimetric titration at a pH 12.5 using as a reference a solution of H$_2$Na$_2$edta and calgonite as an indicator. 20 mL of a solution of H$_4$tpaen (3,10$^{-4}$ M), acidified (pH~2.5) 1:1 Ln:mixture of ligands ([L] 3.10$^{-4}$ M), acidified (pH~2.5) 1:1 Ca:mixture of ligands ([L] 7.10$^{-5}$M) are titrated in a cell with a thermostat (25.0° C.+/−0.1° C.) under Argon after addition of a solution of KOH 0.1 M.

The ionic load was determined with KCl (μ=00.1 M). The titrations have been conducted with a Metrohm 751 GPD Titrino potentiometer fitted with a glass pH electrode. The electrode system was calibrated before each measurement.

The electromotive load is given by the equation E=E°+sp [H$^+$] wherein E° and s are determined by titration of a known amount de HCl with 0.1 M KOH at μ=0.1 M (KCl), using the zone of the acid for the titration. The value used for the ionic product of water was pKw=13.77. More than 50 data points have been collected for each experiment.

Figure 2:
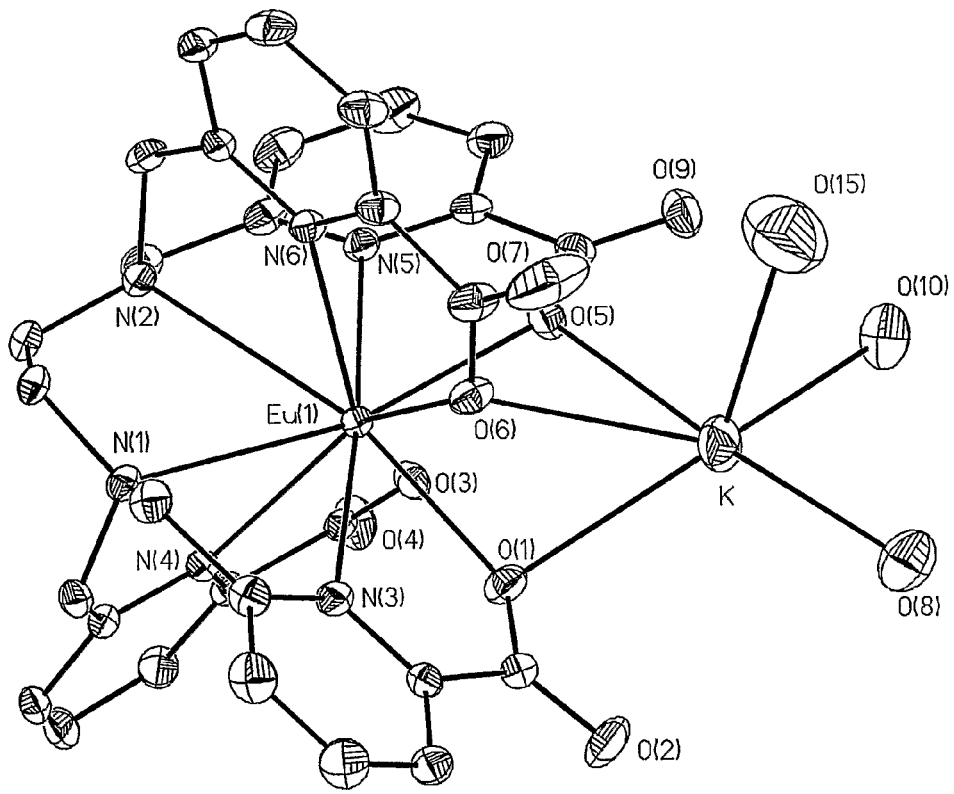
FIG. 2 is a schematic view of an illustration of the molecular structure of a lanthanide complex.
Figure 3:
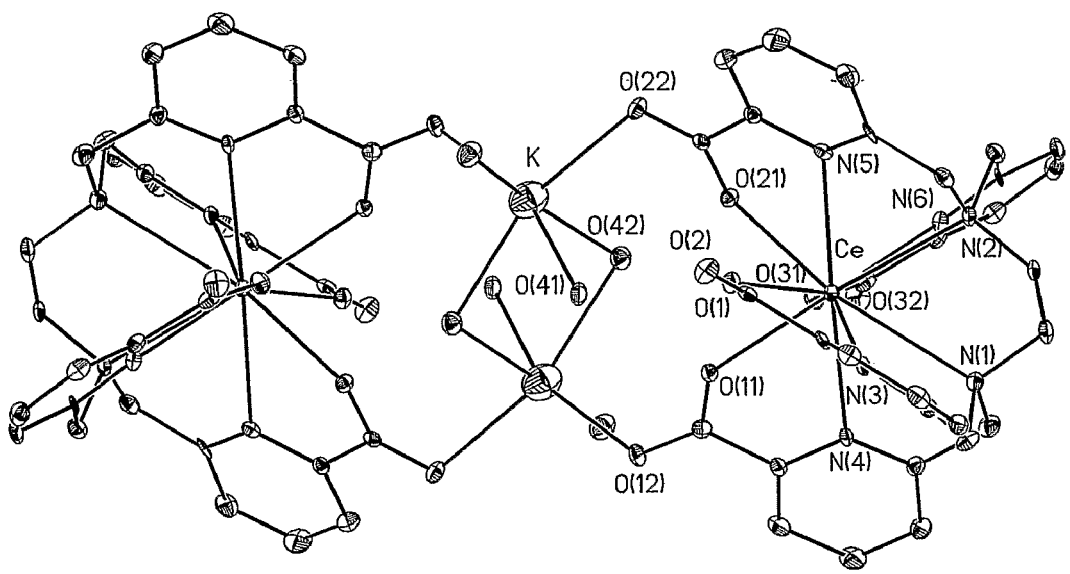
FIG. 3 is a schematic view of an illustration of the molecular structure of a second lanthanide complex.

Moreover, as shown on FIGS. 2 and 3, the crystalline structure respectively of the complexes [Eu(tpaen)]K(H$_2$O)$_3$. 4H$_2$O, and {[Ce(tpaen)]K(H$_2$O)$_3$}$_2$. 16H$_2$O is analysed X-ray diffraction. In both complexes, the ion Ln$^{III}$ s deca-coordinated by the four oxygen atoms (the average value for the distances Metal-0 is 2.42 (1) A for Europium and 2.50 (4) A for Cerium) and by the six nitrogen atoms (the average value for the distances metal-N-pyridine is 2.65 (4) A for Europium and 2.72 (1) Å for Cerium and the average value for the distances metal-N-amine is 2.91 (1) Å for Europium and 2.91 (4) Å for Cerium.

The number of co-ordinated water molecules present in solution, q, was determined from life time measurements using the Parker equation (q=A$_{Ln}$(1/τH$_2$O−1/τD$_2$O−β$_{Ln}$) wherein A$_{Tb}$=5 ms, A$_{EU}$=1.2 ms, αTb=0.06 ms$^{-1}$ and α$_{Eu}$=0.25 ms$^{-1}$). The quantal throughput Q was calculated using the equation Q$_x$/Q$_r$=A$_r$(v).n$_x^2$.D$_x$/A$_x$(v)n$_r^2$.D$_r$ wherein x is the sample, r the reference; A the absorbance, v the number of excitation waves used, n the refractive index, and D the integral of the intensity transmitted.

The complexes of tris(dipicolinate) [Eu(dpa)$_3^{3-}$] (Φ=13.5%, 7.5×10$^{-5}$ M in buffer Tris 0.1 M) and [Tb (dpa)$_3$]$^{3-}$ (Φ=26.5%, 6.5×10$^{-5}$ M in buffer Tris 0.1 M) are used as references respectively for the determination of the quantal throughputs of the samples of Eu- and Tb. The consistency of the data was checked by measuring the quantal throughput of the complexes of the tris(dipicolinate) relative to rhodamine 101 (Q$_{abs}$=100% ethanol) and cresyl violet (Q$_{abs}$=54% methanol).

The chemical and physical analyses of the complexes according to the present invention, show that the "arms" of the pyridine carboxylate moiety of the ligand N,N,N',N'-tetrakis [(6-carboxypyridine-2-yl)methyl]-ethylene diamine surround the central metal in a pseudo symmetrical Ce and helicoidal arrangement.

Both complexes crystallise into a racemic mixture of enantiomers Λ and Δ.

Figure 4:
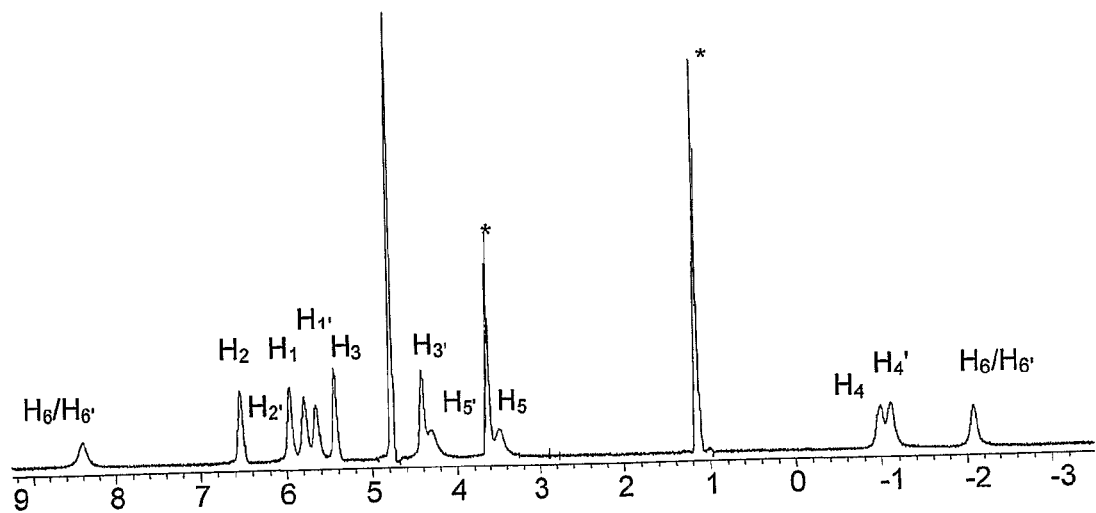
FIG. 4 is a graph illustration of the $^1$H RMN spectrum of a lanthanide complex.

The spectra of nuclear magnetic resonance (RMN) of the Europium and Cerium complexes, as shown on FIG. 4 for the case of the Europium complex with the ligand tpaen at 298 K, show that their structure is compatible with a rigid symmetry C2 wherein the four "arms" of the ligand remain co-ordinated with the metal during the time taken for obtaining the RMN spectrum (*EtoH).

The symmetry observed matches a double-helix chiral structure in solution, similar to that encountered in solid state.

Figure 5:
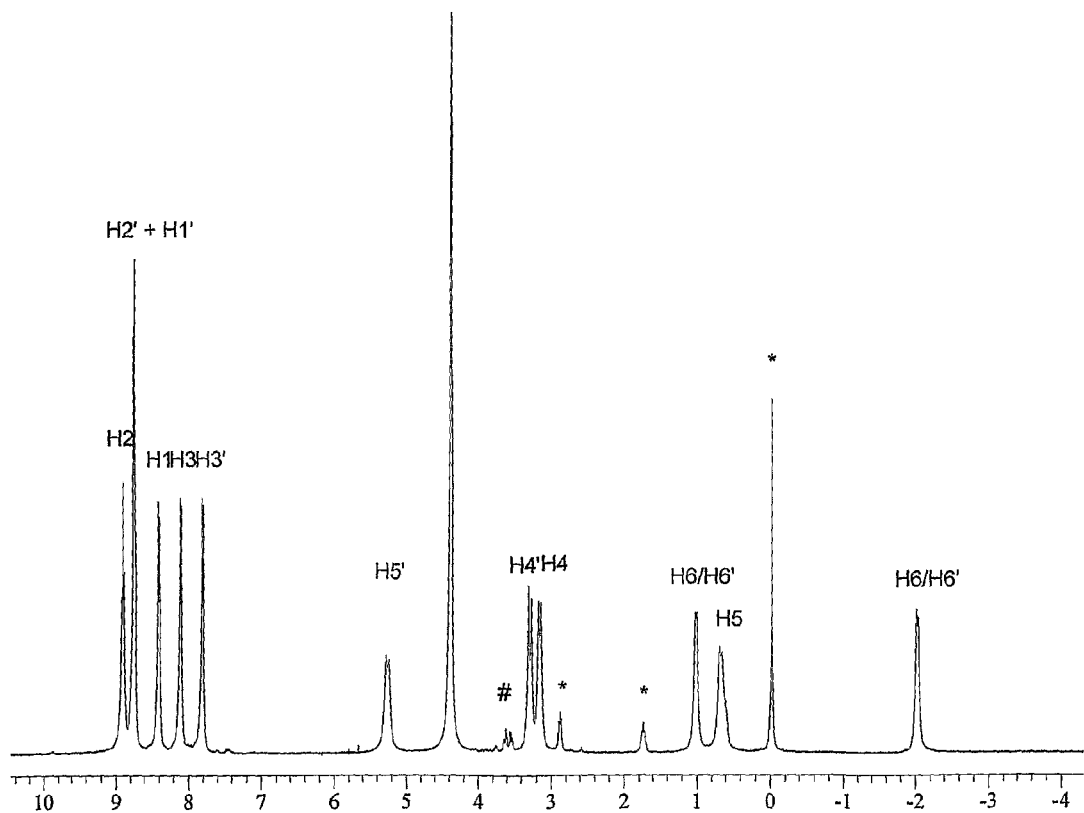
FIG. 5 is a graph illustration of the $^1$H RMN spectrum of a lanthanide complex at 333K.
Figure 6:
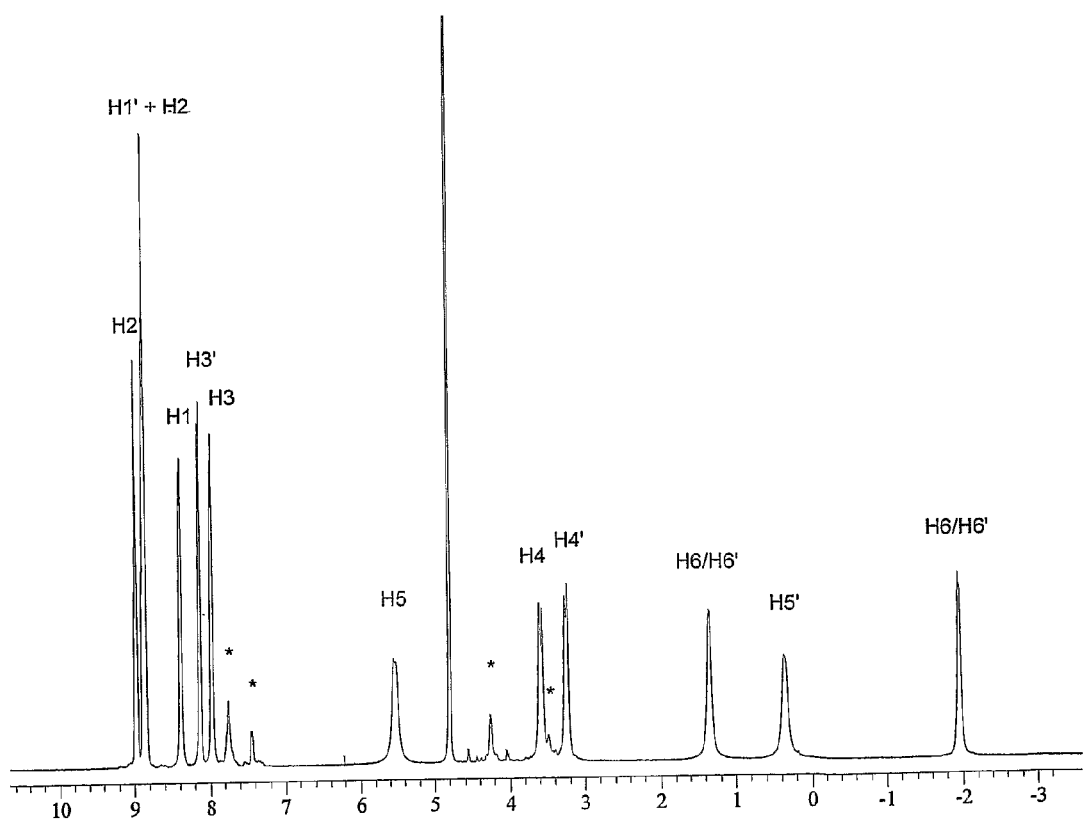
FIG. 6 is a graph illustration of the $^1$H RMN spectrum of a lanthanide complex at 298K.

The complexes keep their rigid structure in a temperature range between 298-363K, as shown by the $^1$H RMN of FIGS. 5 (* DSS; # impurity) and 6 (* free ligand), performed respectively at a temperature of 333 and de 298 K for the particular case of the complex [Ce(tpaen)]-in D$_2$O.

The presence of a rigid symmetry C2 similar to that described above was also observed for the complex of La and Tb prepared in situ in deuterized water to a pH of 7.7. The high stiffness of these complex in solution, very rarely observed for the lanthanide complexes with a high denticity ligand, suggest that the arrangement of the ten donor atoms provided by the simple ethylene diamine chain is well suited to the formation of lanthanide complexes conferring high and efficient protection to the central metal regarding the molecules of the solvents.

As results of this protection, the complex d $Eu^{III}$ and of $Tb^{III}$ with the ligand tpaen exhibit a high luminescence with a long life in water and in deuterized water. The life times of the levels Eu(5Do) and Tb($^5D_4$) for [Eu(tpaen)]" and [Tb(tpaen)]" match the presence of 0.04±0.2 and 0.03±0.2 water molecules co-ordinated respectively in the complexes Eu and Tb.

Figure 7:
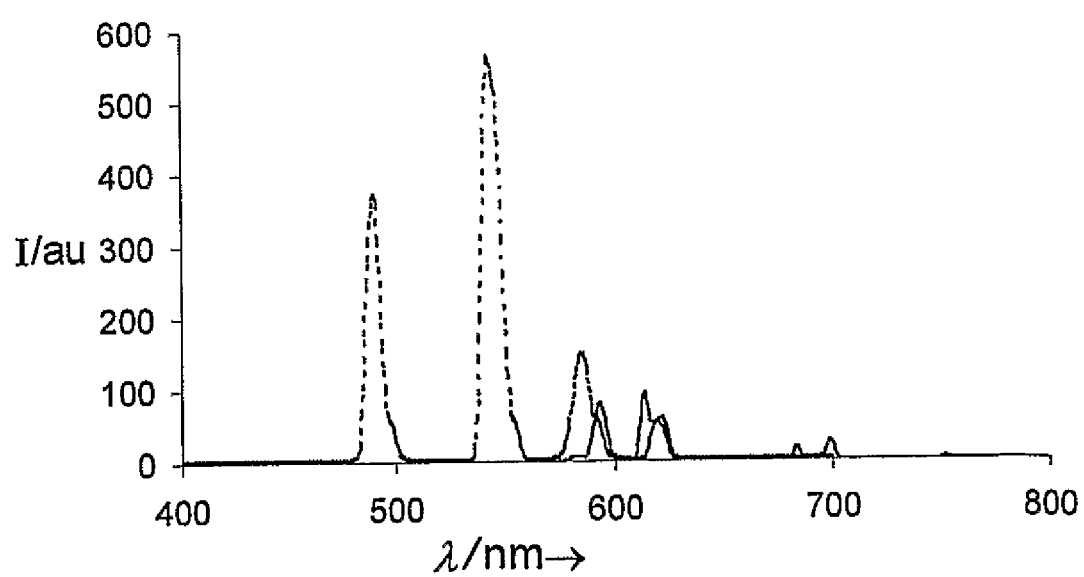
FIG. 7 is a graph illustration of the emission spectrum of two lanthanide complexes after excitation at 274 nm.

The luminescent properties of the lanthanide ions, in particular Eu and Tb, are hence largely improved by the ligand tpaen. FIG. 7 shows the emission spectrum of [Eu(tpaen)] (full line) and [Tb(tpaen)] (dotted line) after excitation of the ligand at 274 nm.

Figure 8:
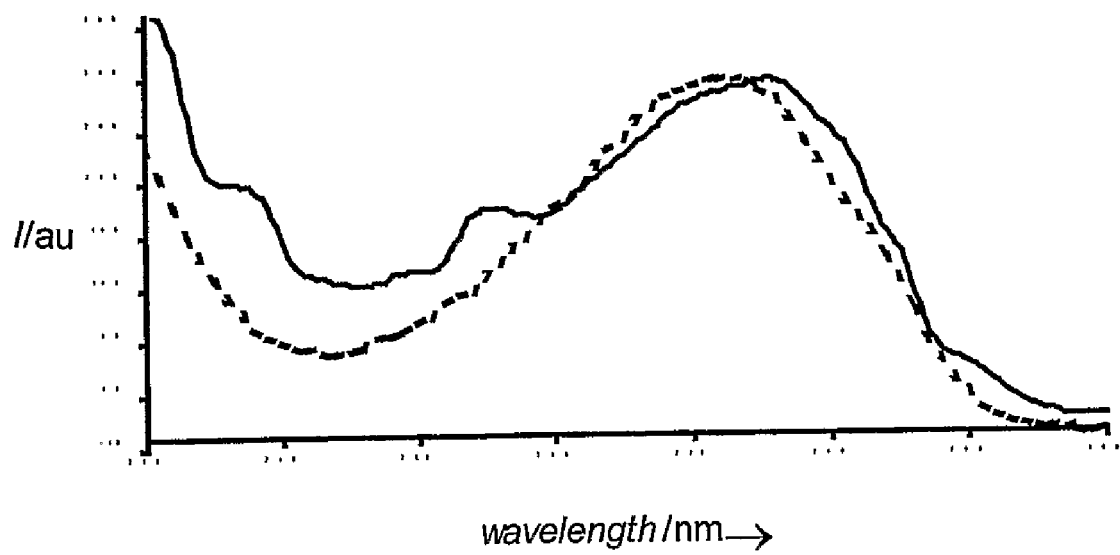
FIG. 8 is a graph illustration of the emission and excitation spectra of a lanthanide.

An efficient energy transfer from the ligand to the metal is put forward by the resemblance between the excitation and absorption spectra of the Europium and Terbium complexes. FIG. 8 shows the absorption spectrum (dotted line) and the excitation spectrum (full line) of the complex of [Tb(tpaen)] in a buffer solution of Tris.

The quantal throughput for the complex of [Tb(tpaen)] ($\Phi$=45%) measured relative to the complex of $[Tb(dpa)_3]^{3-}$ in an aerated buffer solution of Tris of concentration 0.1 M, with a 15% experimental error, is one of the highest values mentioned until now. The chromophore tpaen also sensitises efficiently the Europium ion whereof the value for the quantal throughput is 7%. This value, while smaller than that obtained for the complex of $Tb^{III}$ remains however higher than the quantal throughput of the lanthanide complexes used currently in marketed light-emitting probes.

As shown in the following table, the intense luminescence of these ions results from an efficient energy transfer from the ligand to the metal and from a protection of the central metal relative to non-radiative deactivation by the surrounding water molecules.

| compound | λexc(nm) | $\epsilon(M^{-1}cm^{-1})$ | $\tau_{H2O}$(ms) | $\tau_{D2O}$(ms) | $\Phi_{H2O}$ |
|---|---|---|---|---|---|
| tpaen | 270 | 15800 | | | |
| Eu(tpaen) | 274 | 21600 | 1.70(2) | 3.30(1) | 0.07 |
| Tb(tpaen) | 274 | 21632 | 3.0(1) | 3.75(1) | 0.45 |

The life time of the luminescence observed in the terbium complex in water, to the inventors' knowledge one of the longest observed until now, excludes the presence of a desexcitation process including the return of energy from the metal towards the ligand. This value for the life time is quite compatible with an energy level of the triplet state of the complex [Tb(tpaen)] similar to that divulged recently, (22988 $cm^{-1}$,) for the complex of an octavalent ligand including two pyridine carboxylate moieties. The high quantal throughput for the terbium complex matches this value quite well.

The co-ordinating complexes according to the present invention exhibit several advantages. On the one hand, this direct approach to arrange four divalent chromophores in a decadentate ligand produces highly soluble lanthanide complexes which are stable at a physiological pH. On the other hand, the architecture of the ligand leads to a rigid structure wherein the central metal is protected effectively from the interactions with the molecules of the solvent.

Moreover, this approach opens a wide variety of perspectives for the development of the stable and luminescent probes in the zone of the ultraviolet-visible, infrared and near-infrared, using these compounds, prepared preferably from chromophores transmitting a luminescence in the zone of the ultraviolet or of the near-infrared for a usage in medical imaging and in bio-assays. More generally the medical field, particularly that of the medical analyses seems to be able to benefit from the invention. Besides, the compounds as described in the present application may be anchored with certain functional moieties capable of binding to biomolecules in order to develop markers for luminescence imaging. The complexes may incorporate recognition functions such as dendrimers or also be bound to peptides, oligonucleotides, polymers, nanotubes.

The invention thus also relates to a biomolecule anchored on a complex according to claim, in particular to serve as a luminescent probe. The complexes according to claim, because of their properties, may be used in the nanotechnological industry and in particular in nanotechnological devices such as diodes or optical fibres.

Naturally, other embodiments, understandable to the man of the art, could have been contemplated without departing from the framework of the invention.

I claim:

1. A luminescent transition metal coordinating complex of general formula (I):

$$\{[M(L)]X(H_2O)_n\}_p$$

wherein M represents Europium or Terbium, wherein L represents a decadentate chromophore ligand which is N,N,N',N'-tetrakis[(6-carboxypyridin-2-yl)methyl]ethylenediamine, wherein X represents a counter-ion belonging to the group 1A of the periodic table of the elements, wherein n is from 0 to less than 20, wherein p is 1, and wherein $H_2O$ represents the molecules of hydration water.

2. The luminescent transition metal coordinating complex according to claim 1, wherein the counter-ion is potassium.

3. A luminescent transition metal coordinating complex according to claim 1 further comprising a biomolecule attached thereto.

4. A light-emitting probe for medical-imaging or bio-assays, comprising the luminescent transition metal coordinating complex according to claim 1.

\* \* \* \* \*